United States Patent
Schlun

(10) Patent No.: US 8,152,842 B2
(45) Date of Patent: Apr. 10, 2012

(54) SELF-EXPANDING STENT

(75) Inventor: Martin Schlun, Herxheim bei Landau-Pfalz (DE)

(73) Assignee: C. R. Bard, Inc., Murray Hill, NJ (US)

(*) Notice: Subject to any disclaimer, the term of this patent is extended or adjusted under 35 U.S.C. 154(b) by 208 days.

(21) Appl. No.: 12/438,102

(22) PCT Filed: Aug. 14, 2007

(86) PCT No.: PCT/EP2007/058415
§ 371 (c)(1),
(2), (4) Date: Feb. 19, 2009

(87) PCT Pub. No.: WO2008/022949
PCT Pub. Date: Feb. 28, 2008

(65) Prior Publication Data
US 2010/0234936 A1 Sep. 16, 2010

(30) Foreign Application Priority Data
Aug. 21, 2006 (GB) .................................. 0616579.9

(51) Int. Cl.
*A61F 2/82* (2006.01)
(52) U.S. Cl. .................... 623/1.2; 623/1.22; 623/1.15
(58) Field of Classification Search .................. 623/1.15, 623/1.16, 1.17, 23.7; *A61F 2/06*
See application file for complete search history.

(56) References Cited

U.S. PATENT DOCUMENTS

| | | |
|---|---|---|
| 5,091,205 A | 2/1992 | Fan |
| 5,824,059 A | 10/1998 | Wijay |
| 6,053,940 A | 4/2000 | Wijay |
| 6,241,762 B1 | 6/2001 | Shanley |
| 6,270,524 B1 | 8/2001 | Kim |
| 6,355,057 B1 | 3/2002 | DeMarais et al. |
| 6,475,233 B2 | 11/2002 | Trozera |
| 6,562,065 B1 | 5/2003 | Shanley |
| 6,605,110 B2 | 8/2003 | Harrison |
| 6,770,089 B1 | 8/2004 | Hong et al. |

(Continued)

FOREIGN PATENT DOCUMENTS

DE 102004045994 A1 3/2006

(Continued)

OTHER PUBLICATIONS

Nov. 30, 2007 International Search Report in International Application No. PCT/EP2007/058415 filed on Aug. 14, 2007.

(Continued)

*Primary Examiner* — Thomas J Sweet
*Assistant Examiner* — Jason-Dennis Stewart
(74) *Attorney, Agent, or Firm* — Rutan & Tucker, LLP

(57) ABSTRACT

A self-expanding stent comprising a series of zig-zag stenting rings (A, B, C, D, E, F, D1, D2) spaced along the axis and with adjacent said rings connected by connecting links (12, 14) spaced around the circumference of the rings, the links (12) between any two axially adjacent rings A, B being circumferentially staggered relative to the links (14) between the rings B and C, each ring being constituted by a succession of alternating struts (18) with points of inflection (16, 16', 16") therebetween. The points of inflection at one end of at least one of the rings are staggered in their location along the longitudinal axis whereby, with axial withdrawal of a surrounding sheath at a stenting site, to deploy the self-expanding stent, the individual points of inflection at said one ring end escape from the sheath sequentially, with continued withdrawal of the sheath, rather than simultaneously.

19 Claims, 2 Drawing Sheets

U.S. PATENT DOCUMENTS

| | | |
|---|---|---|
| 6,827,734 B2 | 12/2004 | Fariabi |
| 6,979,346 B1 | 12/2005 | Hossainy et al. |
| 7,772,659 B2 | 8/2010 | Rodmacq et al. |
| 2002/0007212 A1 | 1/2002 | Brown et al. |
| 2002/0116044 A1 | 8/2002 | Cottone et al. |
| 2002/0116051 A1 | 8/2002 | Cragg |
| 2002/0198589 A1 | 12/2002 | Leong |
| 2003/0055485 A1 | 3/2003 | Lee et al. |
| 2003/0225448 A1 | 12/2003 | Gerberding |
| 2004/0073290 A1 | 4/2004 | Chouinard |
| 2004/0073291 A1 | 4/2004 | Brown et al. |
| 2004/0117002 A1 | 6/2004 | Girton et al. |
| 2004/0230293 A1 | 11/2004 | Yip et al. |
| 2005/0149168 A1 | 7/2005 | Gregorich |
| 2005/0182477 A1 | 8/2005 | White |
| 2005/0184277 A1 | 8/2005 | Su et al. |
| 2005/0222667 A1 | 10/2005 | Hunt |
| 2006/0030934 A1 | 2/2006 | Hogendijk et al. |
| 2009/0204201 A1 | 8/2009 | Wack |
| 2010/0016949 A1 | 1/2010 | Wack |
| 2010/0211161 A1 | 8/2010 | Dreher |
| 2010/0249903 A1 | 9/2010 | Wack et al. |
| 2010/0298921 A1 | 11/2010 | Schlun et al. |

FOREIGN PATENT DOCUMENTS

| | | |
|---|---|---|
| EP | 0481365 A1 | 4/1992 |
| EP | 0870483 A2 | 10/1998 |
| EP | 1029517 A2 | 8/2000 |
| EP | 1034751 A2 | 9/2000 |
| EP | 1190685 A2 | 3/2002 |
| EP | 1245203 A2 | 10/2002 |
| EP | 1767240 A1 | 3/2007 |
| WO | 9417754 A1 | 8/1994 |
| WO | 9626689 A1 | 9/1996 |
| WO | 9820810 A1 | 5/1998 |
| WO | 9938457 A1 | 8/1999 |
| WO | 9949928 A1 | 10/1999 |
| WO | 9955253 A1 | 11/1999 |
| WO | 0045742 A1 | 8/2000 |
| WO | 0049971 A1 | 8/2000 |
| WO | 0101889 A1 | 1/2001 |
| WO | 0132102 | 5/2001 |
| WO | 0176508 A2 | 10/2001 |
| WO | 0249544 A1 | 6/2002 |
| WO | 03055414 A1 | 7/2003 |
| WO | 03075797 | 9/2003 |
| WO | 2004019820 A1 | 3/2004 |
| WO | 2004032802 A2 | 4/2004 |
| WO | 2005067816 A1 | 7/2005 |
| WO | 2005104991 A1 | 11/2005 |
| WO | 2006010636 A1 | 2/2006 |
| WO | 2006010638 A1 | 2/2006 |
| WO | 2006025847 A2 | 3/2006 |
| WO | 2006047977 A1 | 5/2006 |
| WO | 2006064153 A1 | 6/2006 |
| WO | 2007073413 A1 | 6/2007 |
| WO | 2007131798 A1 | 11/2007 |
| WO | 2007135090 A1 | 11/2007 |
| WO | 2008025762 A1 | 3/2008 |
| WO | 2008055980 A1 | 5/2008 |
| WO | 2008119837 A2 | 10/2008 |

OTHER PUBLICATIONS

Nov. 30, 2007 Written Opinion of the ISA in International Application No. PCT/EP2007/058415 filed on Aug. 14, 2007.

Feb. 24, 2009 International Preliminary Report on Patentability in International Application No. PCT/EP2007/058415 filed on Aug. 14, 2007.

PCT/EP2007/004407 filed May 16, 2007 International Preliminary Report on Patentability dated Sep. 29, 2008.

PCT/EP2007/004407 filed May 16, 2007 Search Report dated Sep. 26, 2007.

PCT/EP2007/004407 filed May 16, 2007 Written Opinion dated Sep. 26, 2007.

PCT/EP2007/054822 filed on May 18, 2007 International Preliminary Report on Patentability dated Nov. 18, 2008.

PCT/EP2007/054822 filed on May 18, 2007 Search Report dated Sep. 18, 2007.

PCT/EP2007/054822 filed on May 18, 2007 Written Opinion dated Nov. 18, 2008.

PCT/EP2007/058912 filed on Aug. 28, 2007 International Preliminary Report on Patentability dated Nov. 5, 2008.

PCT/EP2007/058912 filed on Aug. 28, 2007 Search Report dated Nov. 12, 2007.

PCT/EP2007/058912 filed on Aug. 28, 2007 Written Opinion dated Nov. 12, 2007.

PCT/EP2007/062155 filed on Nov. 9, 2007 Search Report dated Mar. 12. 2008.

PCT/EP2007/062155 filed on Nov. 9, 2007 Written Opinion dated Mar. 12, 2009.

PCT/EP2007/062155 filed on Nov. 9, 2007 International Preliminary Report on Patentability dated Oct. 15, 2008.

PCT/EP2008/054007 filed Apr. 3, 2008 International Preliminary Report on Patentability dated Jul. 27, 2009.

PCT/EP2008/054007 filed Apr. 3, 2008 Search Report dated Jan. 30, 2009.

PCT/EP2008/054007 filed Apr. 3, 2008 Written Opinion dated Jan. 30, 2009.

U.S. Appl. No. 12/301,019, filed Feb. 2, 2009 Final Office Action dated Feb. 7, 2011.

U.S. Appl. No. 12/301,019, filed Feb. 2, 2009 Non-Final Office Action dated Sep. 3, 2010.

U.S. Appl. No. 12/514,177, filed May 8, 2009 Non-Final Office Action dated Jan. 5, 2011.

U.S. Appl. No. 12/594,531, filed Oct. 2, 2009 Non-Final Office Action dated Dec. 17, 2010.

SELF-EXPANDING STENT

TECHNICAL FIELD

This invention relates to self-expanding stents with a lumen and a longitudinal axis and which exhibit a series of zig-zag stenting rings spaced along the axis, the rings being connected by connecting links that are spaced around the circumference of the rings. Such a stent includes a sequence of three stenting rings A, B and C, with the links between any two axially adjacent rings A and B being circumferentially staggered relative to the links between rings B and C. Each stenting ring is formed out of a succession of alternating struts with points of inflection at the strut ends. These points of inflection form a sequence extending around the circumference of the ring, so that at each axial end of each ring there is a plurality of points of inflection spaced around the circumference and facing the next adjacent stenting ring. Occasionally, two facing points of inflection are connected, by one of the connecting links.

BACKGROUND ART

Typically, a self-expanding stent built up of a stack of zig-zag stenting rings is released from its catheter delivery system by proximal withdrawal of a surrounding sheath relative to the stent. Typically, there is within the catheter delivery system a form of a "stopper" that restrains the stent from moving proximally with the sheath, during the time when the sheath is being pulled back proximally.

In consequence, the distal end annulus of the sheath slides proximally over the full length of the stent, from the distal end of the stent to the proximal end of the stent, in order to release the stent into the body at the stenting site.

The stent being self-expanding, it is pressing on the luminal surface of the surrounding sheath. Stent portions escaping from the restraint of the sheath, as the distal end of the sheath slides proximally past them, will spring radially outwardly. The portion of the stent that is escaping from confinement in the sheath, continues to expand radially outwardly with increasing distance from the retreating end annulus of the sheath, until it presses against the tissue defining the bodily lumen to be stented at the stenting site.

When the stent is composed of a stack of zig-zag stenting rings, with only a few links connecting adjacent stenting rings, the end annulus of the retreating sheath will experience a cyclically varying hoop stress and pattern of radially outward pressure from the matrix of the stent confined within the sheath. Specifically, the forces imposed by the stent on the distal end annulus of the sheath tend to vary cyclically, as each one of the sequence of stenting rings passes the open distal end of the sheath. WO 2004/032802 A2 and EP 1 767 240 A1 address this behaviour.

FIGS. 1a and 1b of WO 2004/032802 A2 show a stent matrix formed of a plurality of interconnected stenting rings. The stenting rings are formed of repeating units of six struts arranged in V-shaped pairs between the links by which adjacent stenting rings are connected. At one axial end of each ring, the points of inflection between the struts in each pair are obliquely staggered in one direction relative to the stent longitudinal axis. Links are formed on the middle ones of these staggered groups of three pairs. The end struts in the repeating units are at one circumferential side of the unit much longer and at the other circumferential side of the unit much shorter than the other four struts in the repeating unit. The long and short struts connect to an adjacent stenting ring at the opposite axial end of the stenting ring from the middle links. Stenting rings joined by the middle links have the obliquely staggered inflection points facing each other, so that the oblique staggering between the facing ends matches; whilst the opposite ends are not obliquely staggered, but are aligned with similar non-regularly staggered points of inflection on the facing ends of further adjacent stenting rings. There are no substantial gaps between the ends of adjacent stenting rings, and only two points of inflection between links on the same end of each ring. There are multiple links between each pair of adjacent stenting rings, around the circumference of the stent.

EP 1 767 240 A1 discloses a stent formed of connected stenting rings. The points of inflection at each end of each ring are staggered alternately, at only two longitudinal positions at each end, between each two links, although there are four such points of inflection between each two links. The struts of the stenting rings are not substantially equal in length, but vary between three different lengths to produce the two-level longitudinal staggering on both ends of the stenting ring.

The behaviour of such stents can be contrasted with the situation where the same delivery system is used to deploy a self-expanding stent that is based not on a stack of stenting rings but on a continuous helical stack pattern of strut end points of inflection. In such a case, given a smooth and stepless withdrawal of the sheath, there will be a steady succession of escapes of points of inflection from the distal end of the sheath, with no two points of inflection escaping at precisely the same moment. It can be appreciated that such a helical stent is not likely to exhibit any significant tendency to "jump" out of the open distal end of the sheath. Conversely, a stent that exhibits a "stenting ring" format has a greater tendency to emerge from the proximally retreating sheath in a series of small jumps (and maybe with one bigger jump as the proximal end of the stent finally escapes from the distal end of the sheath).

It is one object of the present invention to improve the release behaviour of a series of stenting rings from a retreating sheath.

Often, a stent which is in the nature of a series of axially spaced endless stenting rings will have a greater capability to push bodily tissue radially outwards than will a stent that exhibits the form of a continuous helix or spiral from one end of the stent to the other. This greater capability to push radially outwardly of course can raise the amount of force imposed by the stent on the distal end annulus of the retreating sheath and thereby increase the tendency of such a stent to jump distally away from the retreating sheath.

DISCLOSURE OF INVENTION

According to the present invention there is provided a self-expanding stent of the type described above and which is characterised in that the points of inflection at one end of at least one of the stenting rings are staggered in their location along the longitudinal axis of the stent whereby, with axial withdrawal of a surrounding sheath of a stenting site, to deploy the self-expanding stent, the individual points of inflection at said one ring end escape from the sheath sequentially, with continued withdrawal of the sheath, rather than simultaneously.

A stent in accordance with the present invention can be symmetrical or asymmetrical. What is meant by "symmetrical" is that it makes no difference to the performance of the stent which end of the stent is more proximal than the other when the stent is arranged on a delivery system. By contrast, a stent that is "asymmetrical" has a pattern of struts that distinguishes one end of the stent from the other. Intended is that a designated one of the different ends is to be released first from a withdrawing sheath, the opposite end of the stent of course intended to be released last from the sheath. Readers will grasp that passage of the open distal end of the sheath over the stent end that is first to be released does not result in any impulsive forces or tendency of the stent to jump from the sheath. Rather, it is the design of the other axial end of that ring that is released last from the sheath that is significant when it comes to management of impulsive forces in tendency of the stent to jump out of the sheath. Thus, the axial ends of each of the stenting rings of the prosthesis, in particular the one at that end of each ring which is first to escape the sheath, can exhibit points of inflection all on a single plane transverse to the long axis of the prosthesis, without producing any impulsive loading of the sheath during its withdrawal over the length of the stent. By contrast, axial staggering of the points of inflection of that axial end of each stenting ring which is last to be released from the sheath will benefit from axial staggering so that they escape sequentially rather than simultaneously from the retreating sheath.

It is well known that self-expanding stents should be flexible, to bend between straight and arcuate (banana) shapes, both during deployment in the body and after deployment. To meet this need, it is helpful to minimise the number of links between adjacent stenting rings. Thus, a particularly flexible prosthesis can be achieved by reducing to only two the number of links between any two stenting rings, the two links being disposed at opposite ends of a diameter of the prosthesis. Then, advancing along the length of the prosthesis, the links between any two rings should be staggered with respect to the circumferential dispositions of the links between the next adjacent stenting rings. In the case where each pair of stenting rings is linked by only two links, at opposite ends of a diameter (we can say, at 12 o'clock and 6 o'clock when viewed from one end of the stent lumen), the two connectors of the next adjacent rings will conveniently be located at 3 o'clock and 9 o'clock, staggered by half the interval between adjacent links in the next adjacent stenting ring pair.

The invention is not limited to arrangements with two links between adjacent rings. More links are of course possible. If three links are used, they are preferably staggered circumferentially. Thus, if one set of links are at 12, 4 and 8 o'clock then the adjacent sets of links are preferably at 2, 6 and 10 o'clock pointing around the long axis of the stent. The trade off is between the controlled release behaviour of the stent during sheath retraction, improved by having more links, and the desired flexibility of the stent for delivery and in situ, improved by having fewer links.

When an annulus stent matrix is deformed from a straight to an arcuate shape, points of inflection on adjacent stenting rings will approach each other more closely, on the inside of the bend. As the prosthesis arcs out of a straight line, interference between adjacent stenting rings on the inside of the bend can be minimised if the axial staggering of the points of inflection is such that the axial distance between facing points of inflection of adjacent rings increases with circumferential distance off those points of inflection from the links between those rings. In other words, the gap between adjacent rings is bigger, the more circumferentially remote from a link between those adjacent rings.

Of course, adjacent stenting rings may have their adjacent ends arranged so that the staggering of the points of inflection of the linked axial ring ends is in the same direction along the longitudinal axis between the links, without particular loss of flexibility. However, this reduces or closes the gaps or eyelets between the ends of the adjacent stenting rings. For covered stents, such eyelets are desirable, as they allow inner and outer layers of the stent covering material, such as ePTFE, to be joined through the eyelets, thereby encapsulating the stenting rings between the two layers. This provides for superior flexibility than arrangements without such eyelets, for covered stents.

BRIEF DESCRIPTION OF DRAWINGS

For a better understanding of the invention and to show more clearly how the same may be carried into effect, reference will now be made, by way of example, to the accompanying drawings, in which.

BEST MODE FOR CARRYING OUT THE INVENTION

Figure 1:
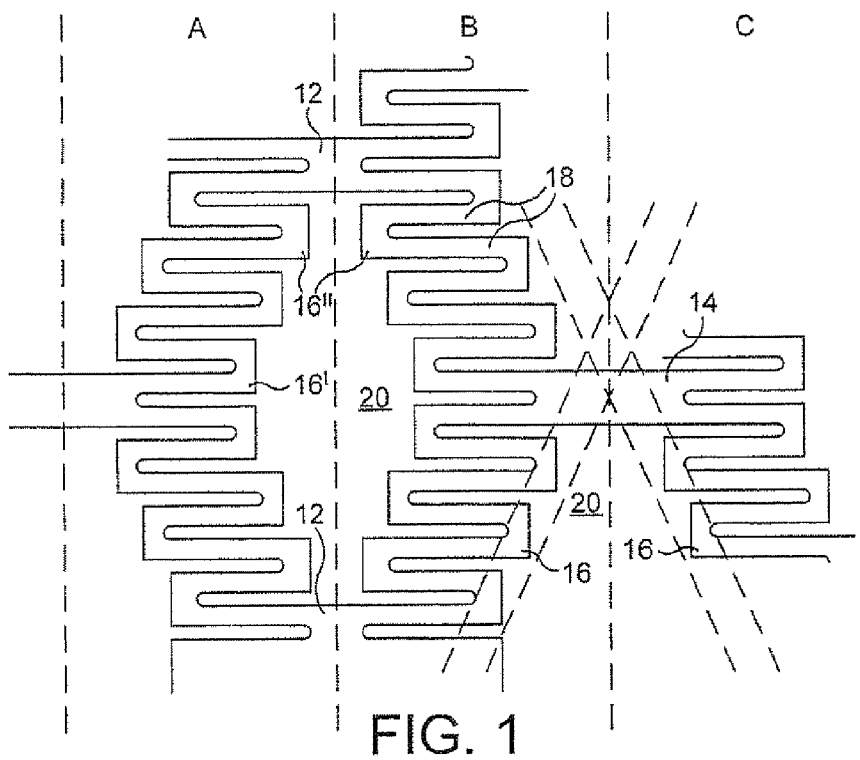
FIG. 1 shows a fragment of the strut matrix of a first embodiment of a stent annulus, opened out flat, to include portions of three axially adjacent stenting rings.

Looking at FIG. 1, portions are shown, of three adjacent stenting rings A, B, C of a stent matrix that features a series of stenting rings with adjacent rings being connected by links. There are two links 12 connecting ring A to ring B and two links 14 (only one of which is visible in FIG. 1) connecting rings B and C. The two links 12 and the two links 14, are respectively disposed at opposite ends of a diameter of the stent annulus. The links 14 are arranged circumferentially halfway between the links 12. Thus, looking at the stent from one end of its lumen, along its longitudinal axis, if the two links 12 are at 12 o'clock and 6 o'clock then the two links 14 are to be found at positions on the annulus corresponding to positions on the clock face of 3 o'clock and 9 o'clock.

Each of the three stenting rings is composed of an alternating string of struts 18 and longitudinally staggered intervening points of inflection 16.

Figure 2:
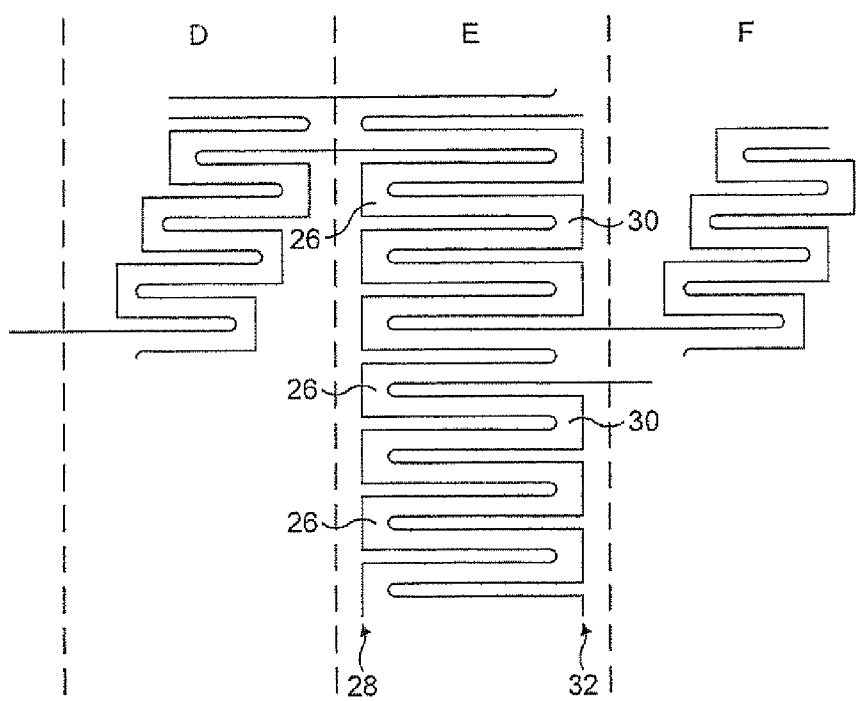
FIG. 2 is a similar view of a second embodiment of a stent.

To achieve the staggering, the struts 18, although of substantially identical length, are arranged with alternately marginally longer and marginally shorter lengths. At each maxima or minima of longitudinal stagger (where a link is, in fact, formed at one end or the other of the stenting ring) the strut length is repeated, rather than alternated, then alternated again on the other side of the link to produce a stagger in the reverse longitudinal direction. In the radially compact delivery disposition of the self-expanding stent, as shown in FIGS. 1 and 2, all the struts 18 are substantially parallel to each other and to the long axis of the stent. Once the self-expanding stent is released from its confining sheath, it self-expands to a radially much larger disposition in which the zig-zags of each stenting ring open up, so that the struts are no longer parallel to each other or to the longitudinal axis of the stent, but are alternatingly sloped obliquely in each direction to the longitudinal axis around the stent circumference.

Whereas points of inflection 16 of adjacent stenting rings are liable to be facing each other across a gap 20 between two adjacent stenting rings, bridged by a link 14 or 12, this is not necessarily the case when the stent expands to its expanded, deployed disposition, depending on any variation of strut length around each stenting ring. After deployment in the body, when a stent is subjected to bending, so that its longitudinal axis becomes arcuate instead of straight, head-to-head contact of points of inflection on the inside of the bend radius is not wanted and can have adverse effects, so any tendency of points of inflection to move past each other, rather than impact head on, is to be welcomed. It can be readily grasped from the fragment shown in drawing FIG. 1 that the relatively large gap 20 between facing points of inflection 16 can be advantageous when it comes to increasing the flexibility of stents in the deployed disposition. If one looks at FIG. 1 and remembers that the two links 12 are at opposite ends of a diameter, then bending of the stent about an axis that passes through the two links 12 at opposite ends of the diameter will bring specific points of inflection 16' closer towards each other. The amount of movement of facing points of inflection towards each other, as the stented, bodily lumen flexes, is reflected by the progressively increasing separation distance of the points of inflection, with circumferential distance away from the link 12. Thus, the distance separating points of inflection 16' is greater than the distance separating points of inflection 16" closer to the link 12. In other words, the separation distance between points of inflection is in proportion to the separation distance needed to accommodate stent bending.

The reader will understand that using a greater number of links spaced around the circumference will dilute the effect, but not lose it altogether. The stenting rings should include a plurality of points of inflection between adjacent links at each axial end thereof, preferably at least three points of inflection or more.

In this way, the distribution of gaps within the stent matrix is corresponding to the gaps needed for stent flexibility and, where smaller gaps can be tolerated without loss of bending capability, smaller gaps are provided. It would seem that a distribution of points of inflection which provides better management of progressive release of stenting rings from the retreating sheath also happens to deliver a better harmony between stent support of the surrounding bodily tissue and stent flexibility as that bodily tissue flexes.

Turning to FIG. 2, portions of three further stenting rings D, E and F are shown. Rings D and F are as described above with relation to FIG. 1, whereas ring E is rather more conventional in that all of its points of inflection 26 at one of its axial ends 28, and all of its points of inflection 30 at the opposite one 32 of its axial ends, lie in a single plane transverse to the longitudinal axis of the stent. They are not axially staggered like the points of inflection of each one of rings A, B, C, D and F. Although in FIG. 2, ring E is shown as an intermediate ring, flanked by rings D and F, another useful purpose for a conventional ring E, with all of its points of inflection in a single plane transverse to the longitudinal axis of the stent is to provide the end of the self-expanding stent prosthesis which is first to emerge from the sheath that withdraws axially to release the stent from its delivery system.

Figure 3:
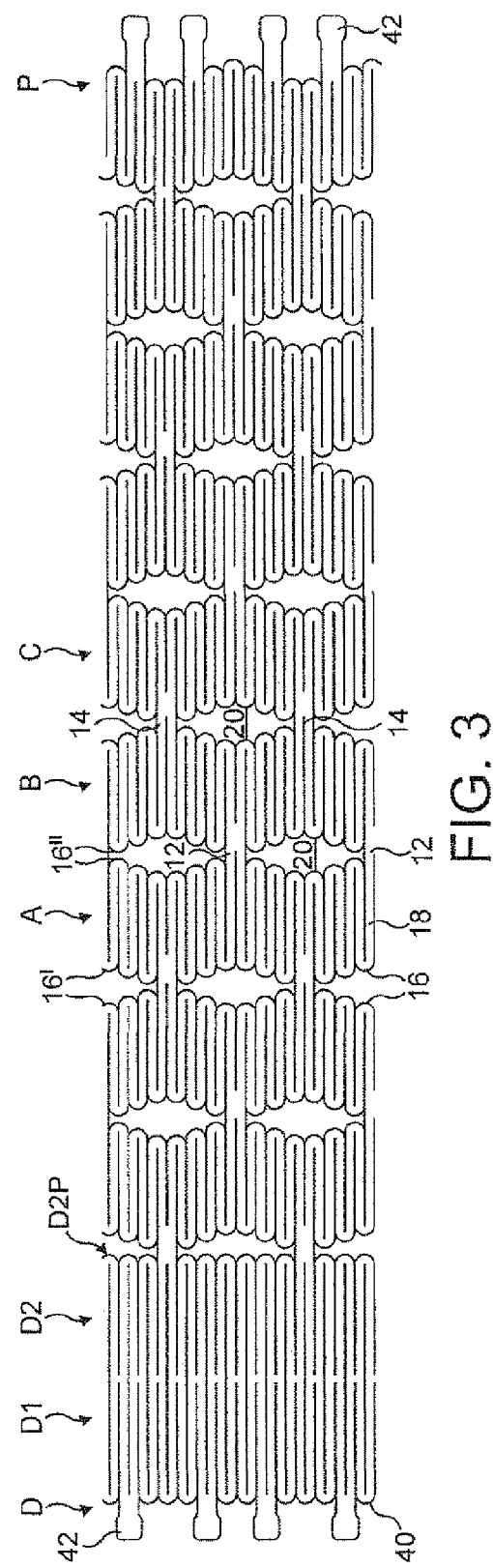
FIG. 3 is a side view of a third embodiment of a stent matrix pattern, in full.

Turning to FIG. 3, reference numbers from FIGS. 1 and 2 are re-used for clarity and economy. Specifically, rings A, B, C are typical of stenting rings all the way along the length of the stent, as far as its proximal end P, the only exception being the last two stenting rings D1 and D2 next to the distal end D of the stent.

The stent is one for release by proximal withdrawal of a restraining sheath. If it were to be released by distal movement of a sheath, then the distal end of the stent would be employed as its proximal end. End D is the one to be released first from the withdrawing restraining sheath.

To be noted about stenting ring D1 is that its terminal points of inflection 40, at the end of the stent D, are all in one plane transverse to the long axis of the stent. In consequence, they all press in the same way, and all together on the confining sheath as it withdraws over the abluminal surface of the stent. This helps to manage uncertainties in the way the polymer material in the distal end annulus of the sheath makes the journey from a location distal of the stent end D to a location proximal of end D. In this journey, it is to be expected that the polymer in the annulus will suffer hoop stress and respond with an elastic strain. This elastic strain should be distributed, to the extent possible, uniformly around the circumference of that annulus under strain.

It is necessary to explain why the stent ring D2 looks like D1 and not like the characteristic ring form A, B, C elsewhere along the stent length.

When the stent of FIG. 3 opens up on deployment from the delivery system and sheath, rings D1 and D2 together form open "diamond" shaped cells with the sides of each diamond being formed by the struts 18. For modelling the fatigue performance of the stent, it is advantageous to have around one circumference of the stent a sequence of diamonds that exhibits a high degree of symmetry. By providing at the proximal end D2P of stenting ring D2 a set of points of inflection that all lie in one plane transverse to the long axis of the stent, that objective can be realised.

The FIG. 3 embodiment shows a set of four projections 42 protruding from each end of the stent. These represent radiopaque markers.

What readers will take from FIG. 3 most clearly is the wave-like character of the axial ends of each stenting ring formed by the lengthwise staggering of the adjacent points of inflection 16, 16', 16" at the axial ends of the rings A, B, C. This approximation to a waveform, preferably to a sinusoidal or triangular waveform, can be tailored to produce a desired variation in the annular hoop stress imparted to the sheath distal annulus as it is withdrawn over the stent.

Moreover, by connecting the distalmost peaks of the waveform at the distal ends of rings B and C with the most proximal peaks of the waveforms at the adjacent proximal ends of rings A and B, respectively, lens-shaped eyelets 20 are formed. With a sinusoidal waveform, these eyelets 20 approach a near-circular or lens shape. For covered stents in particular, these eyelets provide regions through which inner and outer cover layers may be bonded, whilst maintaining the noted flexibility benefited by the plurality of points of inflection 16, 16', 16" between each link 12, 14. Preferably, the plurality of points of inflection 16, 16', 16" between each link 12, 14 defines at least three longitudinal positions, different from the longitudinal position of the links 12, 14. This provides for gradual variations in hoop stresses in the sheath distal annulus during retraction. Preferably, the waveform is regular, with one wavelength between adjacent links 12 or 14, and with an equal number of points of inflection 16, 16', 16" between each peak and trough as between each trough and peak.

On the other hand, the number of points of inflection between each link being preferably 3 or more, and the links being thus well spaced circumferentially about the stent matrix between adjacent rings, the links may be formed peak-to-trough, rather than peak-to-peak as in FIG. 3. This can provide all necessary flexibility for a non-covered stent. Further, if separate linking members are used, rather than directly joining two points of inflection on adjacent ring ends, adjacent rings can be connected trough-to-trough, without losing all flexibility. The linking members must be carefully designed to offer the requisite load bearing capacity whilst allowing the stent to maintain a low profile insertion diameter.

In the present example, the stenting rings are embodied in the form of zig-zag struts. The zig-zag struts may include a repeating pattern made of a unit of, say, four or more generally linear members that extend oblique to the longitudinal axis to intersect each other at three apices spaced apart circumferentially and axially (like an "M" or a "W"). In the present example, the repeating unit is of seven staggered, substantially equally-lengthed, struts between the link at one end of the ring and the next, circumferentially staggered, link at the other end, although the longitudinal staggering direction alternates. Also, the prosthesis can utilize not only the circumferential bridges but also other bridge configurations in combination. Alternatively, the bridge directly connects a peak of one circumferential section to another peak of an adjacent circumferential section. In yet another alternative, the bridge may connect a peak of one circumferential section to a trough of an adjacent circumferential section. In a further alternative, the bridge can connect a trough of one circumferential section to a trough of an adjacent circumferential section.

As noted, the undulations formed at the ring ends by the staggering of the points of inflection can be wave-like in pattern. The wave-like pattern will preferably be generally sinusoidal in that the pattern may have the general form of a sine wave, whether or not such wave can be defined by a mathematical function. Alternatively, any wave-like form can be employed so long as it has amplitude and displacement. For example, a square wave, saw tooth wave, or any applicable wave-like pattern defined by the struts where the struts have substantially equal lengths or unequal lengths. And as used herein, the term "implantable prosthesis" is intended to cover not only a bare stent but also coated, covered, encapsulated, bio-resorbable stent or any portion of similar stents.

Bio-active agents can be added to the prosthesis (e.g., either by a coating or via a carrier medium such as resorbable polymers) for delivery to the bolt's vessel or duct. The bio-active agents may also be used to coat the entire stent. A material forming the stent or coupled to the stent may include one or more (a) non-genetic therapeutic agents, (b) genetic materials, (c) cells and combinations thereof with (d) other polymeric materials.

(a) Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

(b) Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins (nBMP's"), BlVfiP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a EMP can be provided. Such molecules include any of the "hedgehog" proteins, or the DNA"s encoding them.

(c) Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

(d) Suitable polymer materials as a coating or the base material may include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

INDUSTRIAL APPLICABILITY

Stents and covered stents can be manufactured industrially and distributed for use in a wide variety of surgical procedures for treating various medical conditions, inclusive of obstruction of various bodily lumens. Such stents serve to hold open and maintain patent for passage of various bodily fluids, or other matter, such lumens.

The invention claimed is:

1. A self-expanding stent with a lumen and a longitudinal axis, comprising:
a series of zig-zag stenting rings spaced along the axis with adjacent said rings connected by connecting links spaced around the circumference of the rings, the series including:
a sequence of three such rings A, B, C with the links between any two axially adjacent rings A, B being circumferentially staggered relative to the links between the rings B, C,
each ring being constituted by a succession of alternating struts with points of inflection therebetween, there being at each axial end of each ring a plurality of points of inflection on the circumference between any two adjacent links located at that end of the ring,
wherein the points of inflection at one end of at least one of the rings are staggered in their location along the longitudinal axis whereby, with axial withdrawal of a surrounding sheath at a stenting site, to deploy the self-expanding stent, the individual points of inflection at said one ring end escape from the sheath sequentially, with continued withdrawal of the sheath, rather than simultaneously; and
a first leading end stenting ring connected to a second leading end stenting ring, wherein all points of inflection of the first leading stenting ring lie in a first plane transverse to the longitudinal axis, and all points of inflection of the second leading end stenting ring lie in a second plane transverse to the longitudinal axis, and wherein the second leading end stenting ring is connected to a proximally adjacent ring of said series of zig-zag stenting rings via at least two links.

2. The stent according to claim 1, wherein the release behaviour of the stent is the same regardless of which end is released first from the sheath.

3. The stent according to claim 1, further comprising a trailing end stenting ring, to be released last from the sheath, wherein the points of inflection are axially staggered.

4. The stent, according to claim 1, wherein the points of inflection circumferentially furthest from the links are furthest along the longitudinal axis away from the links, escaping from the sheath at a point most distant in time from the point in time when the links escape from the sheath.

5. The stent according to claim 1, wherein all struts in any particular stenting ring, which are separated from a link between that ring and another stenting ring by at least one point of inflection, are substantially the same length.

6. The stent according to claim 1, wherein any two adjacent stenting rings are connected by two links, located at opposite ends of a diameter of the stent lumen.

7. The stent according to claim 1, wherein the links connecting a ring B to the next adjacent ring A at one end of said ring B are substantially staggered with respect to the links to the next adjacent ring C at the other end of the ring B, by half the circumferential interval between the links connecting rings A and B.

8. The stent according to claim 1, wherein the points of inflection at said one ring end are staggered in their location along the longitudinal axis so as to approximate a wave function of longitudinal position around the circumference.

9. The stent according to claim 8, wherein connecting links are formed between said one ring end and an adjacent ring at the points of inflection corresponding with either the peaks or troughs of said wave function.

10. The stent according to claim 9, wherein the points of inflection at the end of the adjacent ring to which said one ring end is connected are staggered in their location along the longitudinal axis so as to approximate a wave function of longitudinal position around the circumference, the links between the one ring end and the end of the adjacent ring being formed at either the peaks or troughs of the wave function of the end of the adjacent ring.

11. The stent according to claim 10, wherein each wave function is substantially the same wave function.

12. The stent according to claim 8, wherein the points of inflection at each end of the three stenting rings A, B and C are staggered in their location along the longitudinal axis so as to approximate a wave function of longitudinal position around the circumference, with the links between adjacent stenting rings being formed between the peaks or troughs of the wave functions of adjacent stenting ring ends.

13. The stent according to claim 8, wherein each wave function is substantially sinusoidal.

14. The stent according to claim 8, wherein the plurality of points of inflection between any two links, defining each wave function, correspond to one wavelength.

15. The stent according to claim 8, wherein the plurality of points of inflection between any two adjacent links, defining each wave function, define at least three longitudinal positions different from the longitudinal position of the links.

16. The stent according to claim 8, wherein the links between each stenting ring end whose points of inflection are formed as an approximation to a waveform and the next stenting ring have a common longitudinal position.

17. The stent according to claim 8, wherein each stenting ring end formed as a waveform creates, as between itself and the end of an adjacent stenting ring to which it is connected, two or more eyelets around the circumference of the adjacent stenting rings, when in an unexpanded configuration, where the peaks and troughs of the waveform result in regions between the linked stenting rings substantially devoid of stent material.

18. The stent according to claim 17, further comprising:
an outer layer surrounding the abluminal surface of at least the region between one or more such linked stenting rings including an end approximating a waveform; and a corresponding inner layer surrounded by the luminal surface of the stenting rings, the inner layer and outer layer being joined together through said eyelets between the stenting rings.

19. A self-expanding stent with a lumen and a longitudinal axis, comprising:

a series of zig-zag stenting rings spaced along the axis with adjacent said rings connected by connecting links spaced around the circumference of the rings, the series including:

a sequence of three such rings A, B, C with the links between any two axially adjacent rings A, B being circumferentially staggered relative to the links between the rings B, C, each ring including a succession of alternating struts with points of inflection therebetween, there being at each axial end of each ring a plurality of points of inflection on the circumference between any two adjacent links located at that end of the ring, wherein the points of inflection at one end of at least one of the rings are staggered in their location along the longitudinal axis so as to approximate a wave function of longitudinal position around the circumference, wherein each stenting ring end formed as a waveform creates, as between itself and the end of an adjacent stenting ring to which it is connected, two or more eyelets around the circumference of the adjacent stenting rings, when in an unexpanded configuration, where the peaks and troughs of the waveform result in regions between the linked stenting rings substantially devoid of stent material, the two or more eyelets forming a lens shape.

* * * * *